United States Patent [19]

Hopkins

[11] Patent Number: 4,752,564
[45] Date of Patent: Jun. 21, 1988

[54] FERMENTATION METHOD AND APPARATUS

[75] Inventor: Thomas R. Hopkins, Bartlesville, Okla.

[73] Assignee: Phillips Petroleum Company, Bartlesville, Okla.

[21] Appl. No.: 513,186

[22] Filed: Jul. 12, 1983

[51] Int. Cl.[4] .......................... C12Q 3/00; C12N 1/34; C12N 1/32; C12N 1/06
[52] U.S. Cl. ........................................ 435/3; 435/246; 435/247; 435/259; 435/804; 435/812
[58] Field of Search ................... 435/246, 804, 812, 3, 435/247, 259, 813, 173

[56] References Cited

U.S. PATENT DOCUMENTS

| 3,355,296 | 11/1967 | Perkins et al. ................ 435/246 X |
| 3,677,895 | 7/1972 | Hashimoto ........................ 435/246 |
| 3,752,742 | 8/1973 | Jaekel et al. ........................ 195/109 |
| 3,886,046 | 5/1975 | Young et al. ................... 435/812 X |
| 3,961,080 | 6/1976 | Sugimoto et al. ............. 435/259 X |
| 3,962,042 | 6/1976 | Malick ................................ 195/143 |
| 3,982,998 | 9/1976 | Hitzman et al. ..................... 195/49 |
| 4,082,611 | 4/1978 | Cotton ............................. 435/804 X |
| 4,145,445 | 3/1979 | Hitzman ............................... 426/60 |
| 4,148,691 | 4/1979 | Malick .................................. 195/42 |
| 4,181,576 | 1/1980 | Malick ................................ 435/247 |

FOREIGN PATENT DOCUMENTS

| 510051 | 5/1980 | Australia . |
| 610797 | 10/1948 | United Kingdom ................ 435/246 |
| 1214957 | 12/1970 | United Kingdom ................ 435/246 |
| 1353008 | 5/1974 | United Kingdom . |
| 1370892 | 10/1974 | United Kingdom . |
| 1417486 | 10/1975 | United Kingdom . |
| 1417487 | 10/1975 | United Kingdom . |
| 1470861 | 4/1977 | United Kingdom ................ 435/812 |

OTHER PUBLICATIONS

Gunsalus, "Extraction of Enzymes from Microorganisms", *Methods in Enzymology*, Academic Press Inc., 1955, vol. I, p. 51.

Primary Examiner—Robert J. Warden
Assistant Examiner—Randall E. Deck
Attorney, Agent, or Firm—Williams, Phillips & Umphlett

[57] ABSTRACT

A process for the production of microbial cells by fermentation of carbonaceous material in a foam fermenter containing an oxygen-enriched nutrient medium. The process uses a source of carbon which is assimilable by the microorganism for the production of the microbial cells. The microbial cells are separated and removed from the foam fermenter for use as a food product high in protein content. The process includes the controlled release of a quantity of the constituents of a portion of the microorganism within the fermenter to increase the maintenance of the source of carbon and the nutrient medium in a foamed condition at a predetermined level in the fermenter. Also disclosed are various forms of apparatus for practicing the process of the present invention.

18 Claims, 4 Drawing Sheets

FERMENTATION METHOD AND APPARATUS

The present invention relates generally to the propagation of microbial cells by the fermentation of carbonaceous material. In one aspect the invention relates to a process for the propagation of alcohol assimilating microbial cells by the aerobic culturing of a suitable microorganism which can assimilate alcohol as the main source of carbon. In another aspect the present invention relates to apparatus for performing the propagation of alcohol assimilating microbial cells by the aerobic culturing of a suitable microorganism which can assimilate alcohol as the main source of carbon.

Current and estimated future worldwide food shortages have encouraged research and development of methods of producing high quality, low cost microbial protein, i.e., single cell protein, to alleviate such food shortages. Considerable development work in fermentation processes has been directed toward the use of hydrocarbons and other carbonaceous materials which would normally be flared or otherwise, disposed of in petroleum refining. The use of methanol as the main source of carbon in such fermentation processes has been particularly attractive because of the advantages offered thereby. Such advantages include the miscibility of methanol with water, the ease and economy with which mentanol can be produced from a wide range of hydrocarbon materials, the ease with which methanol can be produced in virtually any area of the world having any form of fossil fuel supplies, and the absence of potentially carcinogenic polycyclic hydrocarbons when methanol is used as the main source of carbon.

The process of the present invention can be generally characterized as the aerobic fermentation of a suitable carbon source assimilable by a microorganism in fermentors which operate under essentially foam-filled conditions. Suitable sources of carbon material include any feed which can be used to make organisms or their bio-products by a high-cell density foam fermentation process, and include, for example, alcohols, glucose, sucrose (molasses), etc. Such bio-products can include, for example, r-DNA products such as interferon, growth hormones, etc. In one aspect, the carbon source is an alcohol which is assimilated by a suitable microorganism for the production of microbial cells which can be used as a food source (single cell protein). It has been found that fermentation carried out in a foam-filled fermentor in certain fermentation processes is highly efficient when carried out in a continuous process. The foamed contents of the fermentor can be described as the dispersion of the gaseous phase within the liquid phase, or occasionally may be described as an emulsified gaseous phase or simply as an emulsion of the gaseous and liquid phases wherein increased surface area contact is effected between the gas and liquid phases for enhancing the fermentation process. Specifically, it has been found that the fermentation productivity (grams of cells per liter of mixture per hour) is significantly higher when using the foam fermentor than when a conventional paddle stirred tank fermentor is employed.

Fermentation vessels suitable for the formation and maintenance of the contents in a foamed state are known in the fermentation art. Generally, such vessels are those which provide vigorous agitation to the contents with concommitant introduction of some free oxygen-containing substances, such as air, to the mixture. In carrying out the process, small amounts of surfactants can also be employed to aid in the formation and maintenance of the foam. This is not, however, usually required since it is known that many microbial growth processes involve the formation of materials (cellular or extracellular) which have surfactant properties and thus induce foaming. In those instances where the nature of the microbial processes result in less than optimum formation and maintenance of foam, and the use of surfactant additives is not desirable, other means must be sought to enhance the formation and the maintenance of foam to the optimum level in the fermentor vessels.

In accordance with the present invention, the formation and maintenance of foam in foam fermentation processes is enhanced by suitably treating a portion of the microorganisms in the fermentation vessel so as to release or cause the release of the constituents of said thus treated microorganisms. In one aspect, a portion of the microorganisms can be killed. In another aspect, a portion of the microorganisms can be altered so as to rupture or otherwise disrupt the membranes thereof to release the constituents of the microorganisms into the fermentor. The microorganisms can be killed by any suitable means such as the exposure of the microorganisms to high heat, high pH or low pH. The membranes of such microorganisms can be ruptured or disrupted by suitable means such as exposing the microorganisms to high frequency vibration and mechanical shearing, to chemicals normally fed to the fermentation process or to pH-control chemicals.

It is, therefore, an object of the present invention to provide improved process and apparatus for the production of microbial cells.

Another object of the present invention is to provide a process for the foam fermentation of carbonaceous material wherein the formation and maintenance of foam is optimized.

Yet another object of the present invention is to provide improved apparatus for performing foam fermentation which is simple, economical and efficient in operation.

Still another object of the present invention is to provide an improved foam fermentation process which is simple, economical and efficient.

Other objects, aspects and advantages of the present invention will become apparent to those skilled in the art upon further reference to this specification, the appended claims and the accompanying drawings in which:

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting but merely as a basis for the claims and as a representative basis for teaching one skilled in the art to variously employ the present invention in virtually any appropriate manner.

Figure 1:
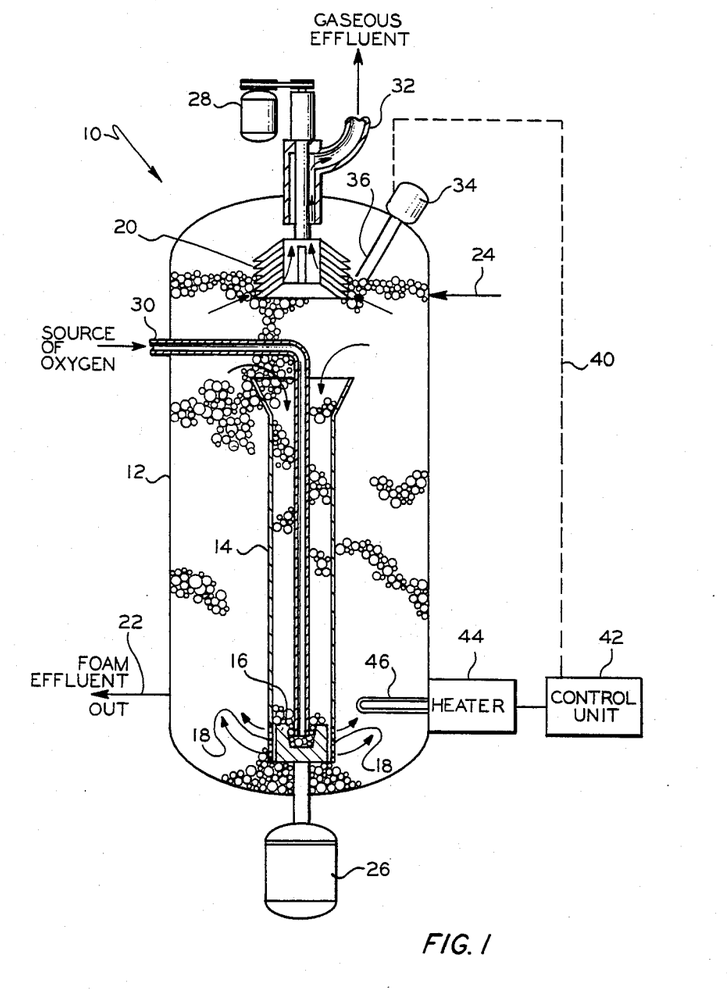
FIG. 1 is a schematic representation of fermentation apparatus illustrating one embodiment of the present invention.

Referring now to the drawings, FIG. 1 illustrates fermentation apparatus generally designated by the reference character 10. The apparatus 10 comprises a closed fermentation vessel 12 having a hollow interior. A draft tube 14 is disposed within the vessel 12 and provides a flow path for the medium contained within the vessel 12 to help induce circulation. A suitable pump such as turbine 16 is positioned within the lower end portion of the draft tube 14 and functions to induce flow downwardly through the draft tube and through emulsifying sieves, in the form of apertures 18 extending through the wall of the draft tube, to the exterior of the draft tube and upwardly therefrom through the anulus between the draft tube 14 and the wall of the vessel 12. A foam breaker 20 is positioned within the upper end portion of the vessel 12 and functions to break foam which might otherwise accumulate in the upper portion of the vessel 12. An outlet 22 communicates with the interior of the lower end portion of the vessel 12 and provides means for drawing off a portion of the contents of the vessel for further processing. The outlet 22 is preferably a conduit which connects the lower end portion of the vessel 12 to secondary processing equipment (not shown). An inlet 24 communicates with the interior of the upper portion of the vessel 12 and provides means for delivery of portions of the nutrient medium used in the fermentation process. Power means such as motors 26 and 28 are respectively operatively connected to the turbine 16 and foam breaker 20 for power operation thereof. A conduit 30 extends through the wall of the vessel 12 and downwardly through the draft tube 14 terminating at a point adjacent the turbine 16. The conduit 30 provides means for introducing a source of oxygen, such as free oxygen, air, or air supplemented by free oxygen, into the medium. An outlet 32 communicates with the interior of the upper end portion of the vessel 12 at a point above the foam breaker 20 and provides means for exhausting gaseous effluent from the fermentation process being carried on within the vessel 12.

A suitable foam level transducer 34 is mounted at the upper end portion of the vessel 12 and provides means for sensing the level of foam within the vessel 12 and providing a suitable signal output in response to the thus sensed level of the foam. While any suitable conventional means for sensing the level of foam within the vessel 12 can be employed as the transducer 34, the foam within the vessel 12 can be employed conductivity electrodes 36 which extend into the vessel and are adapted to close an electrical circuit in the transducer when contacted by foam and open the electrical circuit when their contact with the foam is broken. The output signal from the foam level transducer 34 is transmitted by a suitable conduit 40 to a control unit 42. A heater 44 is mounted on the lower end portion of the vessel 12 and is provided with a heating element 46, such as, for example, a resistance wire or a Calrod ® element.

In the present invention, the fermentation process is carried out with a straight chain alcohol having from 1 to 16 carbon atoms per molecule. This is referred to as the feedstock and is assimilable by the microorganism and supplies the carbon and energy for the microbial growth. Preferably the alcohol has from 1 to 6 carbon atoms per molecule and more preferably the alcohol will be either ethanol or methanol and most preferably will be methanol. Examples of suitable alcohols include methanol, ethanol, 1-propanol, 1-butanol, 1-octanol, 1-dedecanol, 1-hexadecanol, 2-propanol, 2-butanol, 2-hexanol, and the like. Mixtures of two or more such alcohols can also be employed if desired.

The microorganism used in the fermentation process is capable of assimilating one or more of the above alcohols as the source of carbon and energy in the growth or propagation of the microorganism. Suitable microorganisms can be selected from bacteria, yeast and fungi.

Suitable yeasts include species from the genera Candida, Hansenula, Torulopsis, Saccharomyces, Pichia, Debaryomyces, Lipomyces, Cryptococcus, Nematospora, and Brettanomyces. The preferred genera include Candida, Hansenula, Torulopsis, Pichia, and Saccharomyces. Examples of suitable species of yeast include those listed below.

Candida boindinii
Candida mycoderma
Candida utilis
Candida stellatoidea
Candida robusta
Candida claussenii
Candida rugosa
Brettanomyces petrophilium
Hansenula minuta
Hansenula saturnus
Hansenula californica
Hansenula mrakii
Hansenula silvicola
Hansenula polymorpha
Hansenula wickerhamii
Hansenula capsulata
Hansenula glucozyma
Hansenula henricii
Hansenula nonfermentans
Hansenula philodendra
Torulopsis candida
Torulopsis bolmii
Torulopsis versatilis
Torulopsis glabrata
Torulopsis molishiana
Torulopsis nemodendra
Torulopsis nitratophila
Pichia farinosa
Pichia polymorpha
Pichia membranaefaciens
Pichia pinus
Pichia pastoris
Pichia trehalophila
Saccharomyces cerevisiae
Saccharomyces fragilis
Saccharomyces rosei
Saccharomyces acidifaciens
Saccharomyces elegans
Saccharomyces rouxii
Saccharomyces lactis and
Saccharomyces fractum Suitable bacteria include species from the genera Bacillus, Mycobacterium, Actinomyces, Nocardia, Pseudomonas, Methanomonas, Protaminobacter, Methylococcus, Arthrobacter, Methylomonas, Brevibacterium, Acetobacter, Micrococcus, Rhodopseudomonas, Corynebacterium, Rhodopseudomonas, Microbacterium, Achromobacter, Methylobacter, Methylosinus, and Methylocystis. Preferred genera include Bacillus, Pseudomonas, Protaminobacter, Micrococcus, Arthrobacter, and Corynebacterium. Examples of suitable species of bacteria include those listed below.
Bacillus subtilus
Bacillus cereus
Bacillus aureus
Bacillus acidi
Bacillus urici
Bacillus coagulans
Bacillus mycoides
Bacillus circulans
Bacillus megaterium
Bacillus licheniformis
Pseudomonas methanolica
Pseudomonas ligustri
Pseudomonas orvilla
Pseudomonas methanica
Pseudomonas fluorescens
Pseudomonas aeruginosa
Pseudomonas oleovorans
Pseudomonas putida
Pseudomonas borepolis
Pseudomonas pyocyanea
Pseudomonas methylphilus
Pseudomonas brevis
Pseudomonas acidovorans
Pseudomonas methanoloxidans
Pseudomonas aerogenes
Protaminobacter ruber
Corynebacterium simplex
Corynebacterium hydrocarbooxydans
Corynebacterium alkanum
Corynebacterium oleophilus
Corynebacterium hydrocarboclastus
Corynebacterium glutamicum
Corynebacterium viscous
Corynebacterium dioxydans
Corynebacterium alkanum
Micrococcus cerificans
Micrococcus rhodius
Arthobacter rufescens
Arthobacter parafficum
Arthobacter simplex
Arthobacter citreus
Methanomonas methanica
Methanomonas methanooxidans
Methylomonas agile
Methylomonas albus
Methylomonas rubrum
Methylomonas methanolica
Mycobacterium rhodochrous
Mycobacterium phlei
Mycobacterium brevicale
Nocardia salmonicolor
Nocardia minimus
Nocardia corallina
Nocardia butanica
Rhodopseudomonas capsulatus
Microbacterium ammoniaphilum
Archromobacter coagulans
Brevibacterium butanicum
Brevibacterium roseum
Brevibacterium flavum
Brevibacterium lactofermenium
Brevibacterium paraffinolyticum
Brevibacterium ketoglutamicum
Brevibacterium insectiphilium Suitable fungi include species from the genera Aspergillus, Monilia, Rhizopus, Penicillium, Mucor, Alternaria and Helminthosporium. Examples of suitable species of fungi include those listed below.
Aspergillus niger
Aspergillus glaucus
Aspergillus flavus
Aspergillus terreus
Aspergillus itconicus
Penicillium notatum
Penicillium chrysogenum
Penicillium glaucum
Penicillium griseofulvum
Penicillium expansum
Penicillium digitatum
Penicillium italicum
Rhizopus nigricans
Rhizopus oryzae
Rhizopus delemar
Rhizopus arrhizus
Rhizopus stolonifer
Mucor mucedo and
Mucor genevensis The growth of the microorganism is sensitive to the operating temperature of the fermenter and each particular microorganism has an optimum temperature for growth. The broad temperature range employed for the fermentation process of this invention would be from about 30° C. to 65° C. and more preferably between 35° C. and 60° C. The temperature selected will generally depend upon the microorganism employed in the process since they will have a somewhat different temperature/growth rate relationship.

In the practice of the present invention, a suitable nutrient medium is supplied to the fermenter to provide nutrients such as an assimilable source of nitrogen, phosphorus, magnesium, calcium, potassium, sulfur and sodium as well as trace quantities of copper, manganese, molybdenum, zinc, iron, boron, iodine and selenium. As is well known in the art of fermentation, the relative amounts of the above nutrients can vary depending on the microorganism selected for the process. In addition, the nutrient medium can also contain vitamins as is known in the art when their presence is known to be desirable for the propagation of certain microorganisms. For example, many yeasts appear to require the presence of one or both of the vitamins biotin and thiamin for their proper propagation. A typical example of a suitable nutrient medium is shown in the following recipe.

| One Liter Aqueous Solution | |
| --- | --- |
| Component | Amount |
| $H_3PO_4$ (85%) | 2.0 ml |
| KCl | 1.0 g |
| $MgSO_4 7H_2O$ | 1.5 g |
| $CaCl_2 2H_2O$ | 0.2 g |
| NaCl | 0.1 g |
| Trace Mineral Solution | 5.0 ml |

The trace mineral solution as listed in the above recipe is formulated as given in the following recipe.

| One Liter Aqueous Solution (Trace Mineral Solution) | |
| --- | --- |
| Component | Amount |
| $CuSO_4 5H_2O$ | 0.06 g |
| KI | 0.08 g |
| $FeCl_3 6H_2O$ | 4.80 g |

-continued

| One Liter Aqueous Solution (Trace Mineral Solution) | |
|---|---|
| Component | Amount |
| $MnSO_4H_2O$ | 0.30 g |
| $Na_2MoO_42H_2O$ | 0.20 g |
| $ZnSO_47H_2O$ | 2.00 g |
| $H_3BO_2$ | 0.02 g |

When using the nutrient medium described above the source of assimilable nitrogen is supplied by the separate addition of aqueous ammonia ($NH_4OH$) to the fermentation vessel. The amount of $NH_4OH$ added will depend upon the pH desired for the reaction mixture. Without any added $NH_4OH$ the pH will be about 2 for the nutrient medium. Preferably for the utilization of yeasts or fungi in the fermentation process the pH is preferably in the range of approximately 3–5 and for the utilization of bacteria the pH should preferably be in the range of approximately 6–7.5.

The fermentation reaction is an aerobic process wherein the oxygen needed for the process can be supplied from a free oxygen-containing source such as air which is suitably supplied to the fermentation vessel at a pressure of from approximately 1–100 atmospheres and preferably from 1–10 atmospheres. One good source of oxygen is oxygen enriched air. The fermentation reaction is often favorably affected by use of pressure within the above-described broad and preferred ranges.

Preferably the fermentation process of the instant invention is a continuous type but it is to be noted that it can be conducted as a batch process. In the continuous or batch process modes of operation the fermentation reactor is first sterilized and subsequently inoculated with a culture of the desired microorganism in the presence of all the required nutrients including oxygen and the carbon source. In the continuous method of operation the oxygen source or air is continuously introduced along with continuous introduction of nutrient medium, nitrogen source (if added separately) and alcohol at a rate which is either predetermined or in response to need which can be determined by monitoring such things as alcohol concentration, dissolved oxygen, and oxygen or carbon dioxide in the gaseous effluent from the fermenter. The feed rate of the various materials can be varied so as to obtain as rapid a cell growth as possible consistent with efficient utilization of the alcohol feed, i.e., a high yield of cell weight per weight of alcohol feed charged.

As is known in the art, the feed rate of the alcohol is an important variable to control since in high concentration this material can actually inhibit cell growth and may even kill the microorganism. Therefore, the feed rate of the alcohol is adjusted such that the alcohol is consumed by the microorganism at essentially the same rate as it is being fed to the fermenter. When this condition is attained there will be, of course, little or no alcohol in the effluent which is continuously withdrawn from the fermenter in a continuous type of process. However, satisfactory operation can be achieved with up to about 0.5 percent by volume alcohol concentration in the effluent. For high cell productivity or growth rate, the concentration of alcohol in the feed to the fermenter should be from about 7 percent up to about 30 percent by volume.

For batch or continuous operation of the process of this invention, the concentration of feedstock, e.g., methanol, in the fermenter should be within the range of from 0.001 up to 5 percent (v/v) and preferably from 0.005 up to 0.5 percent (v/v). It is possible, of course, and may in some instances be desirable, to add the feedstock incrementally to an otherwise typical batch fermentation process.

It is well known in the art that instrumentation is available to measure cell density, pH, dissolved oxygen and alcohol concentration in the fermenter as well as the feed and effluent streams so as to provide a rather complete monitoring of the fermentation process with the instrumentation being adapted to control the input rates so as to optimize the process. The materials fed to the fermenter are preferably subjected to sterilization as is normally done in the art in order to prevent contamination of the desired fermentation mixture by unwanted viable microorganisms.

The effluent removed from the fermentation vessel is suitably treated for separating the microbial cells, containing single cell protein, therefrom. The usual method of treatment is well known to those in the art and employs the use of heat and/or chemical reagents, e.g., acids, to kill the microbial cells and aid in their separation from the aqueous phase by coagulation or flocculation of the cells. After this treatment the mixture is next centrifuged to remove most of the liquid phase and then the separated cells are further dried such as by drum dryers or spray dryers. If yeast is used as the culture the above sequence of steps can be modified by first centrifuging the effluent to separate the cells which are then killed by heat prior to or during a later drying step. After separation and drying, the cells which contain a high amount of protein are then ready or available for use as a food source by animals and/or humans.

The single cell protein produced by the above process has a particularly important utility in the world today. As has been increasingly emphasized in recent years, the supply of abundant and inexpensive protein available for human or animal consumption such as fishmeal and soya bean meal is being strained by an ever-increasing world population and recent reduction in production of certain types of protein as, for example, fishmeal based on anchovy fishing harvests. The production of single cell protein (SCP) offers a way to alleviate this situation by providing a source of protein suitable for inclusion in the diets of poultry, swine, cattle which directly or indirectly provide protein for humans. The microbial cells produced according to the above process are suitable single cell protein sources and can thus be employed for food purposes. It is known that the protein produced by this process can be employed in other areas such as the production of proteinaceous adhesive compositions, enzymes and other protein products having uses in the health and food science field.

In the operation of the apparatus 10, a suitable amount of nutrient medium and alcohol is fed into the vessel 12 via inlet 24. Turbine 16 is rotated relative to the apertures 18 by means of motor 26 to generate the desired foaming within the vessel 12 and to induce circulation of the thus generated foam within the vessel 12 upwardly through the annulus between the draft tube 14 and the vessel wall and downwardly through the draft tube 14 as shown by the directional arrows. A suitable amount of oxygen is injected through the conduit 30 to the lower portion of the draft tube 14 to further enhance foam formation. When the desired level of foam generation is achieved within the vessel 12, the interior of the vessel is innoculated with a desired microorganism to initiate fermentation therein. During the fermentation process, if the desired foam level within the vessel 12 falls from the predetermined value, the electrodes 36 previously in electrically conductive contact with the upper portion of the foam will no longer be in such contact with the foam thus opening the electrical circuit in the transducer 34 and causing an output signal to be generated by the transducer 34 and transmitted via conduit 40 to control unit 42. In response to this output signal, the control unit 42 will cause the activation of the heater 44 and the resulting heating of the heating element 46 within the lower portion of the vessel 12 thus causing microorganisms coming in contact with or in close proximity to the heated column 46 to be killed thus releasing the constituents thereof to the foam thereby causing enhancement of the foaming within the vessel 12 and thus raising the level of the foam within the vessel 12. When the level of foam within the vessel 12 reaches the desired level, the electrodes 36 previously out of electrically conductive contact with the upper surface of the foam within the vessel will regain electrically conductive contact with the upper surface of the foam thus closing the electrical circuit in the transducer 34 whereby the foam level transducer 34 is caused to generate another signal which is transmitted via conduit 40 to the control unit 42. In response to the second signal, the control unit 42 will cause the heater 44 to turn off thus deactivating the heater element 46 and causing the cessation of killing of microorganisms thereby within the vessel 12.

The apparatus 10 is capable of a continuous process wherein equilibrium is achieved in the fermentation process being carried out therein. When equilibrium is achieved, nutrient and alcohol are continuously fed through the inlet 24 of the vessel 12 at a desired rate and foam effluent containing the desired microbial cells is continuously withdrawn via the outlet 22 for further processing at a remote location by suitable means (not shown). Such suitable processing can include the separation and recovery of the microbial cells from the remaining constituents of the foam effluent as well as recovery of soluble products produced by the microbial cells and released into the fermentor effluent.

Figure 2:
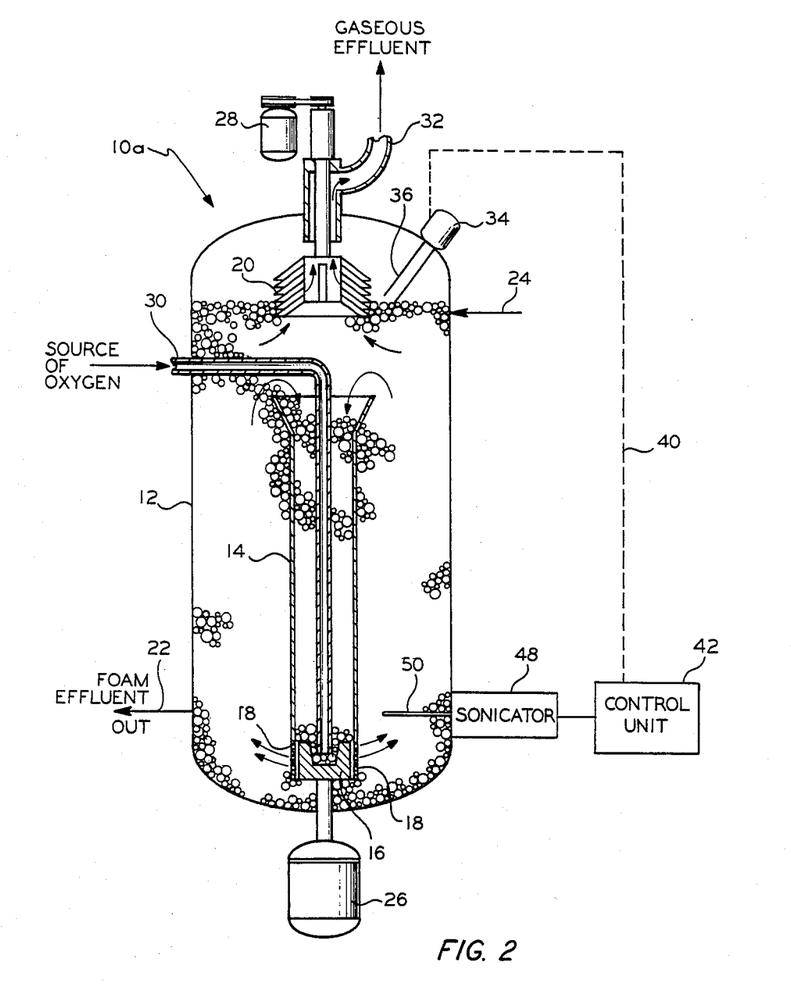
FIG. 2 is a schematic representation of another embodiment of fermentation apparatus in accordance with the present invention.

FIG. 2 illustrates fermentation apparatus 10a which is a slightly modified version of the apparatus 10. Elements of the apparatus 10a which are identical to the previously described apparatus 10 are identified by the same reference numerals. The apparatus 10a differs from the apparatus 10 only in the utilization of a sonicator 48 which is operatively connected to the control unit 42 and which includes a sonication probe 50 which extends from the sonicator 48 through the wall of the vessel 12 into the lower portion of the vessel 12.

The operation of the apparatus 10a differs from the operation of the apparatus 10 only in the activation by the control unit 42 of the sonicator 48 in response to a signal from the foam level transducer 34 of a low level of foam within the vessel 12, and, alternately, the deactivation of the sonicator 48 and the sonication probe 50 in response to a signal from the control unit which in turn responds to a signal from the foam level transducer 34 of a satisfactory level of foam within the vessel 12. When the sonicator 48 is activated by the control unit 42, the sonication probe 50 transmits by vibrations to the contents of the vessel 12 of sufficient frequency and intensity to rupture the membranes of a portion of the microorganisms which come in contact therewith or move into close proximity thereto whereby the constituents of the thus ruptured microorganisms are released within the vessel and provide enhancement for the foam generation occurring therein.

Figure 3:
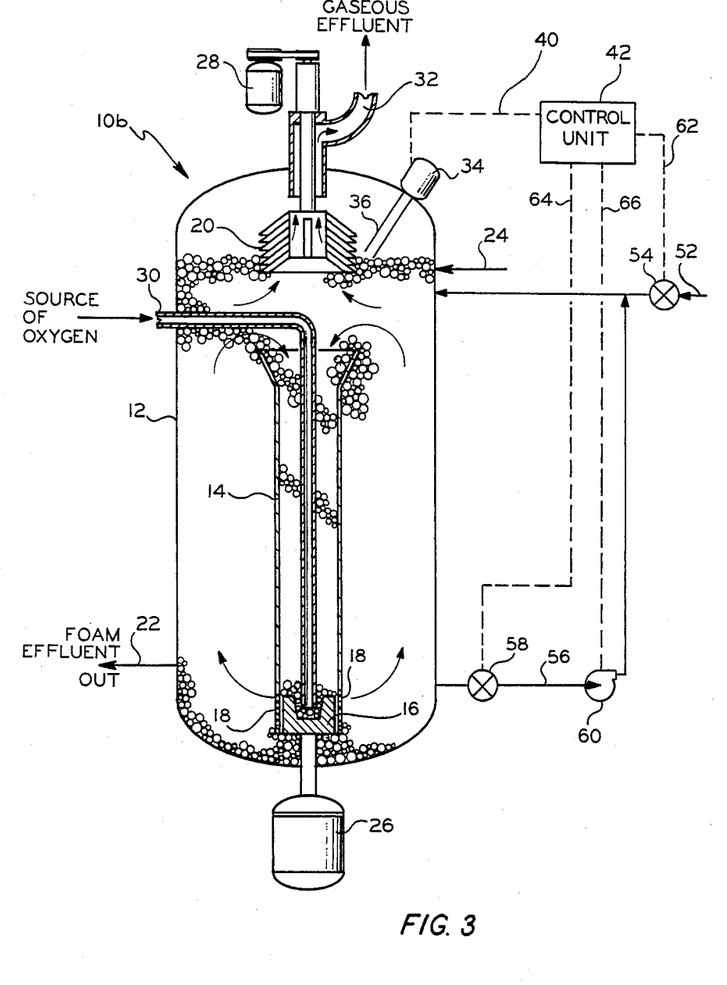
FIG. 3 is a schematic representation of still another embodiment of fermentation apparatus in accordance with the present invention.

FIG. 3 illustrates yet another form of fermentation apparatus designated by the reference character 10b which differs slightly from the previously described apparatus 10. Those elements of the apparatus 10b which are identical to those elements previously described for the apparatus 10 are identified by the same reference numerals.

The apparatus 10b is characterized by a conduit 52 which communicates with the interior of the upper end portion of the vessel 12 via a control valve 54. A second conduit 56 provides fluid flow communication between the interior of the lower portion of the vessel 12 and conduit 52 intermediate the control valve 54 and the upper portion of the vessel 12. A second control valve 58 and a suitable pump 60 are interposed in the conduit 56, with the control valve 58 being positioned proximate the vessel 12. Control conduits 62, 64 and 66 operatively connect the control unit 42 with the control valves 54 and 58 and the pump 60, respectively. Conduit 52 is connected to a suitable source of materials (not shown) which materials are capable of disrupting the membranes of the microorganisms or killing the microorganisms upon contact therewith. Such suitable materials include an alcohol assimilable by the microorganism which is provided at such a controlled alcohol concentration as to disrupt the membranes of the microorganisms contacted thereby and thereby extract lipids from the thus disrupted membranes of the microorganisms. Such alcohol can also be provided at such a controlled concentration as to actually kill the microorganisms contacted thereby. Other suitable materials which can be employed to kill microorganisms contacted thereby include such materials which raise the pH of the medium containing the microorganism to such a level as to kill microorganisms contacted thereby which then results in the release of the constituents of the microorganism through autodigestion in the fermenter. Such suitable materials include, for example, ammonium hydroxide and sodium hydroxide. Similarly, suitable materials for killing microorganisms can also include such materials as lower the pH of the medium carrying the microorganisms to a level which also kills such microorganisms. Such materials include, for example, hydrochloric acid, sulfuric acid and phosphoric acid. Other disrupting agents which may be suitable in the case of non-food products include detergents, chloroform and toluene.

It will be understood that it is necessary to achieve contact between such disruptive materials and only a small portion of the vessel contents at a sufficiently high concentration of such materials to achieve cell disruption. Upon passage back into the bulk of fermentor volume, the disruptive chemical or solvent materials are diluted to an extent sufficient to render the chemical or solvent materials harmless to the remaining cells.

In the operation of the apparatus 10b, when the level of the foam within the vessel 12 falls to a predetermined level, the foam level transducer 34 provides, in the manner previously described, a signal via conduit 40 to control unit 42. In response to the signal, control unit 42 provides actuating signals to the control valves 54 and 58 and the pump 60 which opens the control valves 54 and 58 and actuates the pump 60 to circulate foam from the lower portion of the vessel 12 through the conduit 56 and conduit 52 into the upper portion of the vessel 12 while simultaneously introducing one of the previously discussed materials through the open control valve 54 to disrupt the membranes of or kill at least a portion of the microorganisms thus circulated. The thus killed or disrupted microorganisms then release their constituents within the vessel 12 to thereby enhance the formation of foam therein. When the level of foam within the vessel 12 reaches a predetermined level, the foam level transducer 34 provides an output signal responsive thereto to the control unit 42 which, in turn, causes closing of the control valves 58 and 54 and deactivates the pump 60.

Figure 4:
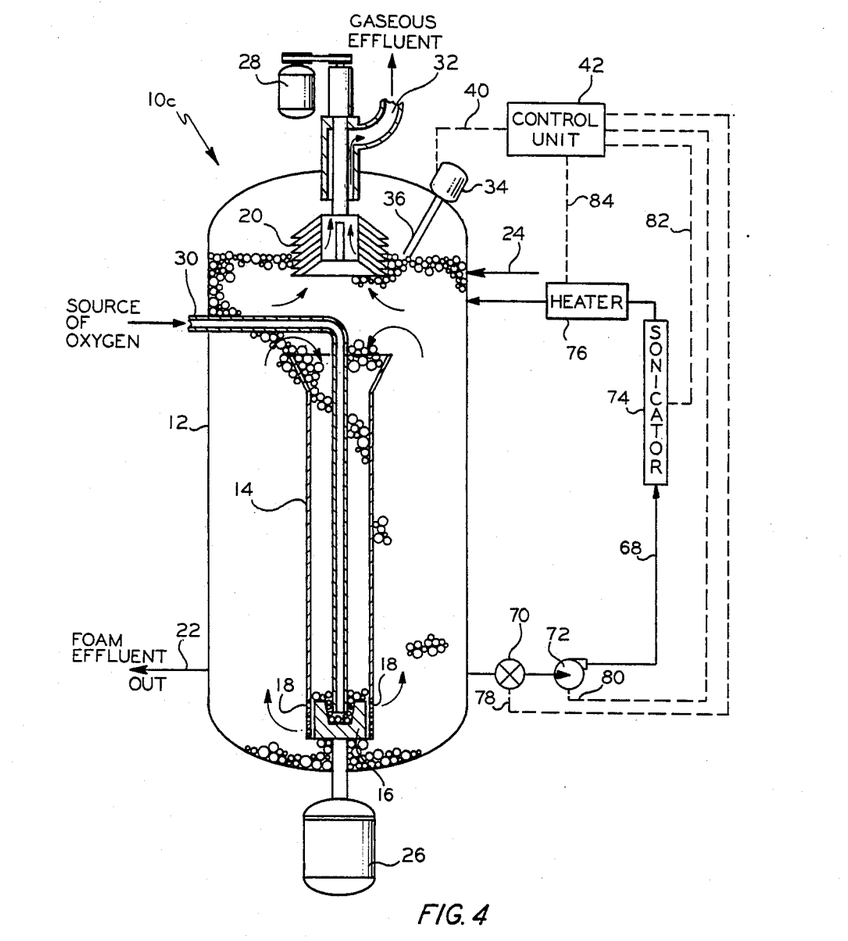
FIG. 4 is a schematic representation of yet another embodiment of fermentation apparatus in accordance with the present invention.

FIG. 4 illustrates another embodiment of the apparatus of the present invention which is generally designated by the reference character 10c. The apparatus 10c is substantially identical to the previously discussed apparatus 10 with identical elements carrying the same reference numerals as employed in the description of the apparatus 10. The apparatus 10c employs a recycle conduit 68 which provides fluid flow communication between the interior of the lower portion of the vessel 12 and the interior of the upper portion of the vessel 12. Interposed in the conduit 68 are a control valve 70, a pump 72, a sonicator 74 and a heater 76. Control conduits 78, 80, 82 and 84, respectively operatively connect the control unit 42 to the control valve 70, pump 72, sonicator 74 and heater 76. In operation of the apparatus 10c, when the foam level transducer 34 provides an output signal via conduit 40 to the control unit 42 indicating an excessively low level of foam within the vessel 12, the control unit 42 provides signals via conduits 78 and 80 to the control valve 70 and pump 72 to cause the control valve 70 to open and to actuate the pump to circulate foam from the lower portion of the vessel 12 to the upper portion of the vessel 12 via conduit 68, sonicator 74 and heater 76. The control unit also causes the activation of the sonicator 74 and/or the heater 76 to cause disruption of the membranes of a portion of the microorganisms passing through the conduit 68 or to cause the killing of at least a portion of the microorganisms passing through the conduit 68. The sonicator 74 functions in the same manner as the previously described sonicator 48 although the output of the sonicator 74 is applied only to the contents of the conduit 68. Similarly, the heater 76 functions in the same manner as the previously described heater 44 except that the heater 76 applies its heat only to those microorganisms circulating through the conduit 68. As in the previous embodiments of the apparatus, the constituents of those microorganisms which have been either killed or disrupted are introduced into the interior of the vessel 12 to enhance the formation of foam therein. When the foam within the vessel 12 reaches the desired level, the foam level transducer 34 provides a suitable signal via conduit 40 to the control unit 42 which, in turn, causes the closure of the control valve 70 and deactivation of the pump 72, sonicator 74 and/or heater 76.

Changes may be made in the process or in the combination and arrangement of parts or elements in the various embodiments of the present invention as heretofore set forth in the specification and shown in the drawings without departing from the spirit and scope of the invention as defined in the following claims.

That which is claimed is:

1. A process for the production of microbial cells, said process including the steps of:

placing a microorganism into a fermentor containing a nutrient medium and aerobically culturing said microorganism, said microorganism being capable of assimulating a carbonaceous material as a main source of carbon;

introducing a carbonaceous material into said fermentor as the main carbon source for said microorganism to assimilate and produce microbial cells;

maintaining said carbonaceous material and said medium in a foamed condition in said fermentor so that said fermentor is essentially foam-filled;

causing the release of a quantity of the constituents of a portion of said microbial cells within the fermentor to sustain said carbonaceous material and said medium in said foamed condition at predetermined level; and separating and recovering the microbial cells produced in said fermentor.

2. A process in accordance with claim 1 wherein said constituents are released from said microbial cells by killing said portion of the microbial cells within the fermentor and allowing the constituents of the killed microbial cells to be released within the fermentor.

3. A process in accordance with claim 2 wherein said portion, of the microbial cells are killed within the fermentor by subjecting said portion of the microbial cells to heat.

4. A process in accordance with claim 2 wherein said portion of the microbial cells are killed within the fermentor by contact between the microbial cells and a heating element disposed within said fermentor and maintained at a temperature sufficient to kill microbial cells coming in contact therewith.

5. A process in accordance with claim 1 wherein said constituents are released from said microbial cells by rupturing the membranes thereof to release the constituents contained within the membranes to the interior of the fermentor.

6. A process in accordance with claim 5 wherein said membranes are ruptured by application of vibration thereto.

7. A process in accordance with claim 5 wherein said membranes are ruptured by the application of mechanical shearing thereto.

8. A process in accordance with claim 1 wherein said carbonaceous material comprises an alcohol having from 1 to 16 carbon atoms per molecule.

9. A process in accordance with claim 1 further comprising the step of recovering soluble products produced by said microbial cells and released into the fermentor.

10. A process in accordance with claim 1 wherein said constituents are released from said microbial cells by withdrawing a stream containing microbial cells from said fermentor and killing said portion of the microbial cells contained within said stream to provide killed microbial cells and thereafter recycling said stream and said killed microbial cells back into said fermentor thereby allowing release of the constituents of said killed microbial cells within said fermentor.

11. A process in accordance with claim 10 wherein said portion of the microbial cells in said stream are killed by subjecting the microbial cells in said stream to a temperature sufficient to kill such microbial cells.

12. A process in accordance with claim 10 wherein said portion of said microbial cells contained in said stream are killed by contacting said stream with a material sufficient to raise the pH of the stream to a level sufficient to kill said portion of the microbial cells therein.

13. A process in accordance with claim 10 wherein said portion of said microbial cells contained in said stream are killed by contacting said stream with a material sufficient to lower the pH of the stream to a level sufficient to kill said portion of the microbial cells therein.

14. A process in accordance with claim 1 wherein said constituents are released from said portion of said microbial cells by withdrawing a stream containing microbial cells from said fermentor and rupturing the membranes of said portion of the microbial cells contained within said stream to release the constituents contained within the membranes to said stream, and thereafter recycling said stream and said microbial cells and released constituents back into said fermentor.

15. A process in accordance with claim 14 wherein said membranes are ruptured by application of vibration thereto.

16. A process in accordance with claim 14 wherein said membranes are ruptured by contacting said microbial cells with an assimilable alcohol at a controlled alcohol concentration sufficient to disrupt the membranes and extract lipids from the thus disrupted membranes of said microbial cells into said stream.

17. A process in accordance with claim 1 wherein said release of a quantity of the constituents of said portion of said microbial cells within the fermentor is controlled by initiating said release in response to the foamed condition of said carbonaceous material and said medium being below said predetermined level, and by terminating said release in response to the foamed condition of said carbonaceous material and said medium being at said predetermined level.

18. A process for the production of microbial cells, said process comprising the steps of:
placing a microorganism in a fermentor, said microorganism being capable of assimilating a straight chain alcohol having from 1 to 16 carbon atoms per molecule as a main source of carbon;
continuously introducing a nutrient medium into said fermentor at a controlled rate;
introducing oxygen into said fermentor continuously at a controlled rate for aerobically fermenting said alcohol;
continuously introducing a straight chain alcohol having from 1 to 16 carbon atoms per molecule into said fermentor at a controlled rate for said microorganism to assimilate as the carbon source and produce microbial cells;
maintaining said fermentor during operation at a pressure of at least about 1 atmosphere;
maintaining said alcohol and said nutrient medium in a foamed condition in said fermentor so that said fermentor is essentially foam-filled;
releasing a quantity of the constituents of a portion of the microbial cells within the fermentor to sustain said alcohol and nutrient medium in said foamed condition in said fermentor so that said fermentor is essentially foam-filled; and
continuously separating and recovering microbial cells produced in said fermentor.

* * * * *